United States Patent
Haar et al.

(10) Patent No.: US 6,584,335 B1
(45) Date of Patent: Jun. 24, 2003

(54) ANALYTICAL DEVICE FOR IN VIVO ANALYSIS IN THE BODY OF A PATIENT

(75) Inventors: Hans-Peter Haar, Wiesloch (DE); Gerhard Werner, Weinheim (DE); Dirk Boecker, Heidelberg (DE); Armin Lambrecht, March (DE); Joachim Kastner, Dortmund (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/485,004

(22) PCT Filed: Aug. 6, 1998

(86) PCT No.: PCT/DE98/02262

§ 371 (c)(1),
(2), (4) Date: May 8, 2000

(87) PCT Pub. No.: WO99/07277

PCT Pub. Date: Feb. 18, 1999

(30) Foreign Application Priority Data

Aug. 9, 1997 (DE) .......................... 197 34 617
Aug. 9, 1997 (DE) .......................... 197 34 618

(51) Int. Cl.[7] ................................. A61B 5/00
(52) U.S. Cl. ............................... 600/322; 600/325
(58) Field of Search ............................. 600/309–310, 600/322–328, 339, 316

(56) References Cited

U.S. PATENT DOCUMENTS

| | | | | |
|---|---|---|---|---|
| 4,270,840 A | * | 6/1981 | Uchida et al. | 350/96.34 |
| 4,502,487 A | * | 3/1985 | DuBrucq et al. | 600/476 |
| 4,530,750 A | * | 7/1985 | Aisenberg et al. | 204/298 |
| 4,622,974 A | * | 11/1986 | Coleman et al. | 600/342 |
| 4,694,832 A | | 9/1987 | Ungerstedt | |

(List continued on next page.)

FOREIGN PATENT DOCUMENTS

| | | | |
|---|---|---|---|
| DE | 40 38 354 C 2 | 6/1992 | G01N/21/01 |
| EP | 0 404 562 A2 | 12/1990 | G01N/21/35 |
| EP | 0 589 862 A2 | 3/1994 | A61B/5/00 |
| WO | WO 90/01697 | 2/1990 | G01N/33/48 |
| WO | WO 91/18548 | 12/1991 | A61B/5/00 |
| WO | WO 93/07469 | 4/1993 | G01N/21/59 |
| WO | WO 95/10223 | 4/1995 | A61B/5/00 |
| WO | WO 96/10198 | 4/1996 | G02B/6/02 |
| WO | WO 97/06426 | 2/1997 | G01N/21/55 |

OTHER PUBLICATIONS

Gobel, et al., "Enhancing the Sensitivity of Chemical Sensors for Chlorinated Hydrocarbons in Water by the Use of Tapered Silver Halide Fibers and Tunable Diode Lasers," Applied Spectroscopy 49:1174–1177 (1995).

(List continued on next page.)

Primary Examiner—Eric F. Winakur
Assistant Examiner—Matthew Kremer
(74) Attorney, Agent, or Firm—Jill L. Woodburn (57) ABSTRACT

Analysis device for determining an analyte in vivo in the body of a patient, having a measuring probe with a hollow needle (18) which can pierce through the skin. Light is passed through the hollow needle (18) and into the body via an optical fiber (22) travelling in the hollow needle (18). The light transported in the optical fiber (22) is modified in the measuring probe (3), the modification being characteristic of the presence of the analyte. A measurement and evaluation unit (4) measures the change to extract information concerning the presence of the analyte in the body. The hollow needle (18) is permeable, at least in a partial section of its length, serving as a measuring section (30) which can be inserted into the skin so that interstitial liquid may penetrate through the hollow needle wall to a measuring section of the optical fiber extending in the hollow needle (18) and the modification of the light characteristic of the presence of the analyte is effected through interaction with the interstitial liquid in the measuring section.

114 Claims, 5 Drawing Sheets

U.S. PATENT DOCUMENTS

| | | | | |
|---|---|---|---|---|
| 4,820,293 | A | * | 4/1989 | Kamme .................... 604/368 |
| 4,846,548 | A | | 7/1989 | Klainer ................... 350/96.29 |
| H704 | H | * | 11/1989 | Di Vita et al. .......... 350/96.23 |
| 4,986,622 | A | * | 1/1991 | Martinez ................ 350/96.15 |
| 5,114,738 | A | * | 5/1992 | Savage et al. ................ 427/37 |
| 5,127,077 | A | | 6/1992 | Iyer et al. .................... 385/116 |
| 5,176,881 | A | * | 1/1993 | Sepaniak et al. ............. 422/82 |
| 5,353,792 | A | | 10/1994 | Lubbers et al. |
| 5,436,454 | A | | 7/1995 | Bornstein et al. ...... 250/339.12 |
| 5,452,716 | A | | 9/1995 | Clift |
| 5,582,184 | A | * | 12/1996 | Erickson et al. ............ 600/576 |
| 5,746,217 | A | * | 5/1998 | Erickson et al. ............ 600/573 |
| 5,949,537 | A | * | 9/1999 | Inman et al. ............... 356/246 |

OTHER PUBLICATIONS

Kastner, et al., "Optimizing the optics for Evanescent Wave Analysis With Laser Diodes (EWALD) for monitoring chlorinated hydrocarbons in water," SPIE 2783:294–306.

Mendelson, et al., "Blood Glucose Measurement by Multiple Attenuated Total Reflection and Infrared Absorption Spectroscopy," IEEE Transactions on Biomedical Engineering 37:458–465 (1990).

Heise, et al., "Multicomponent Assay for Blood Substrates in Human Plasma by Mid–Infrared Spectroscopy and its Evaluation for Clinical Analysis," Applied Spectroscopy 48:85–95 (1994).

Simhi, et al., "Multicomponent Analysis of Human Blood using Fiberoptic Evanescent Wave Spectroscopy," EOS/SPIE Code No 2331–21, 1–7.

Troupe, et al., "Diamond–based glucose sensors," Diamond and Related Materials 7:575–580 (1998).

* cited by examiner

ANALYTICAL DEVICE FOR IN VIVO ANALYSIS IN THE BODY OF A PATIENT

The invention concerns an analysis device for determining an analytic substance in the body of a patient (human or possibly animal) having a measuring probe comprising a hollow needle which can pierce through the skin.

The concentration of components of body fluids (analytes) is almost exclusively determined, in medical applications, by means of reagents. Towards this end, a sample of the body fluid (in particular blood) is taken and analyzed in the laboratory in vitro. The methods are being continuously improved and small hand-held analysis systems have meanwhile become available for important analytes, in particular blood glucose. The methods nevertheless have the disadvantage that each individual investigation requires the removal of blood and continuous measurements are not possible.

Fiber optic chemical sensors (FOCS) are known in the art for continuous measurement via immersion in a sample liquid. The absorption or luminescence of an indicator molecule is thereby observed via an optical fiber, the indicator molecule being localized on the tip of the optical fiber or in a jacket surrounding same. FOCS have also been used for continuous measurements of analytes in the blood of a patient, e.g. using a catheter introduced into the vein. Devices of this type are described in the following publications:

a) U.S. Pat. No. 5,127,077
b) EP 0 589 862 A2
c) U.S. Pat. No. 4,846,548

Efforts have been made for a long period of time to develop primarily based on spectroscopic principles reagent free analysis procedures. Conventional absorption spectroscopy using a transmission measurement is, however, in the major part of the spectrum not possible in blood, since blood contains strongly absorbing substances (in particular hemoglobin) which cover the characteristic spectral bands of the analytes being sought. Even if one removes the hemoglobin using a centrifuge, a strong interfering optical absorption remains in the particularly interesting regions of the infrared spectrum.

For this reason the possibility of using ATR (Attenuated Total Reflection) spectroscopy for investigation of aqueous biological liquids, in particular blood, has been studied. Reference is made to the following publications:

1) Y. Mendelson: "Blood Glucose Measurement by Multiple Attenuated Total Reflection and Infrared Absorption Spectroscopy", IEEE Transactions on Biomedical Engineering, 1990, 458–465.
2) H. M. Heise et al.: "Multi component Assay for Blood Substrates in Human Plasma by Mid-infrared Spectroscopy and its Evaluation for Clinical Analysis", Applied Spectroscopy 1994, 85 to 95.
3) R. Simhi et al.: "Multi-component Analysis of Human Blood Using Fiber Optic Evanescent Wave Spectroscopy", SPIE Proc. Vol. 2331: Medical Sensors II and Fiber Optic Sensors Sep. 6–Sep. 10, 1994, Lille, France, A. V. Scheggi et al. (Eds.), ISBN 0-8194-1664-9, published 1995, pages 166 to 172.

These references show that it is, in principle, possible to use ATR spectroscopy to detect important analytes, in particular glucose, in blood reagent free by spectroscopic means. In ATR spectroscopy, light is transported through a light guide whose outer surface is in contact with the sample. The index of refraction within the light guide (relative to the index of refraction of the sample) and the angles of reflection of the light at the boundary must be selected such that the light is totally internally reflected. Total internal reflection comprises penetration of an evanescent wave into the neighboring medium (the sample). The absorption which thereby occurs leads to an attenuation of the intensity of the light transported in the light guide. This attenuation in intensity can be evaluated as a function of wavelength in order to extract information from the spectrum concerning the presence of the analyte in the sample. Further details can be taken from the relevant literature, in particular, 1) to 3) cited above.

ATR measurements generally utilize special ATR measuring cells with a light guide having a prismatic shape. Alternatively, fiber optic light guides have been frequently proposed. An example, with regard to medical analysis of blood components, is reference 3).

The publication
4) U.S. Pat. No. 5,436,454,
describes a device which allegedly enables ATR spectroscopy of blood of a patient in vivo. Towards this end, a thin hollow needle, similar to an injection needle, can be introduced through the skin of the patient into a blood vessel for in vivo measurements. A thin optical fiber passes through the hollow needle up to the tip thereof and is bent at this location back in the opposite direction in a narrow loop to travel back through the hollow needle. A light guide leg passing through the hollow needle transports measuring light to the loop. A second leg passes the light back to a detector. The hollow needle has a diameter of approximately 3 mm and an inner bore of approximately 2 mm for acceptance of the optical fibers having a diameter of 0.7 mm to 1 mm. The publication discloses that many more reflections of the light transported in the light guide occur in the region of the loop than in the straight sections. As a result thereof, a substantially higher sensitivity is present in the loop region. In the measurement state, the loop protrudes somewhat past the tip of the hollow needle and a seal prevents the sample from penetrating into the hollow needle. The measurement is thereby confined solely to the region of the loop. The measurement is intended to be carried out in a spectral region having wave numbers between 7,000 and 700 (corresponding to 1.5 to 15 $\mu$m). Chalcogenic glass is proposed as a material for the optical fibers.

Another example of a publication concerned with ATR spectroscopy for in vivo analysis of body components, in particular glucose, is
5) WO 91/18548.

A further measurement concept, namely the measurement of the index of the refraction, is recommended for measuring glucose in blood in
6) WO 90/101697.

On the basis of this prior art, it is an object of the invention to provide an improved analysis device for determination of an analyte in vivo in the body of the patient.

This purpose is achieved using an analysis device for the determination of an analyte in vivo in the body of a patient, including a measuring probe comprising a hollow needle for puncturing into the skin and with an optical fiber travelling through the hollow needle by means of which light emanating from a light source and coupled into the optical fiber can be guided through the hollow needle to the measuring probe which is pierced into the skin and thus into the body, wherein the light in the measuring probe transported through the optical fiber undergoes, through direct reagent free interaction with interstitial liquid surrounding the optical fiber within in the body, a change characterizing the presence of the analyte and having a measurement and evaluation unit for measuring the change and for deriving, from this change, information concerning the presence of the analyte in the body, characterized in that the hollow needle is permeable through at least a partial section of its length which penetrates into the skin and which serves as a measuring section, so that the interstitial liquid passes through the hollow needle wall and gains access to a measuring section of the optical fiber extending in the hollow needle, and the change in the light characterizing the presence of the analyte results from interaction with the interstitial liquid in the measuring section.

It has been discovered within the context of the invention that in contrast to the recommendation of publication 4) the measurement is advantageously not concentrated at a loop at the tip of the hollow needle. Rather it is carried out along a longer measuring section of preferentially at least 2 mm and particularly preferentially between 3 mm and 10 mm of length within a hollow needle which can be penetrated along the length of this measuring section. The measuring medium is not blood in a vein but rather the interstitial liquid in skin tissue, preferentially in subcutaneous skin tissue. An improved precision and sensitivity is thereby achieved. Among other reasons, it has been discovered in accordance with the invention that a highly localized measurement is associated with a high risk of measurement error due to local irregularities both with regard to the measuring probe as well as with regard to the surrounding skin tissue. In contrast to the FOCS, the analysis is based on the direct reagent-free interaction along the measuring section of the light transported through the optical fiber with the sample liquid.

The measuring section of the hollow needle is sufficiently permeable to the interstitial liquid that the interaction of the light transported in the optical fiber with the analyte which is required for the analysis takes place in the measuring section. Within the context of the invention, it has been discovered that, with the very small dimensions of the hollow needle, diffusion exchange of the analyte between the interstitial liquid surrounding the hollow needle and the surface of the optical fiber in the measuring section is sufficient to allow monitoring of the physiological changes of important analytes, in particular glucose, with high precision. The permeability of the hollow needle must be adapted to this requirement. In the preferred case of a metallic hollow needle, the permeability is effected by appropriate perforations.

In addition to metal, a sufficiently stiff plastic would also, in principle, be suitable for making the needle. In such embodiment the required permeability may result from the structure of the plastic material itself, i.e. a material can be utilized which is permeable to the analyte molecules without subsequent introduction of holes, due to its manufacturing and material properties.

Goals of the invention, in particular to allow measurement precision while maintaining patient acceptance for continuous measurements over long periods of time (at least one day and preferentially three days), can be better achieved when the following preferred features are utilized individually or in combination with each other.

A preferred measurement principle is based on the interaction between the light and the analyte in the measuring section caused by the penetration of an evanescent field into the liquid, in particular based on ATR spectroscopy. Thus the wavelength dependent attenuation in the measuring section is the modification of the light transported in the optical fiber which is characteristic of the presence of the analyte. Concerning suitable measurement and evaluation procedures, reference is made to the complete disclosure of the relevant literature, in particular to the publications cited above.

The wavelength of the measuring light is preferentially in the mid-infrared (MIR), in particular between approximately 7 $\mu$m and 13 $\mu$m. This wavelength region is particularly suitable for the analysis of glucose as the analyte.

The optical fiber material should in the spectral region of the measuring light be as transparent as possible. A silver halide compound, in particular AgCl, AgBr or mixtures thereof, are particularly suitable to achieve the purpose of the invention. Particularly preferred are mixtures having a predominant fraction of AgBr. These materials have very low absorption in the relevant spectral region and can be produced in the form of very thin elastic fibers. A potential problem associated with their use in contact with body liquids is that body liquids always contain substantial concentrations of ions which can corrode the silver halide compound. Within the context of the invention, it has however been determined that silver halide fibers, in particular in the above mentioned wavelength regions, can be used for a period of several days in direct contact with the interstitial liquids without additional protective measures and without having their function being impaired to a significant extent by corrosion.

Use of silver halide fibers for non-medical analysis is e.g. disclosed in the following literature:

7) R. Goebel et al.: "Enhancing the Sensitivity of Chemical Sensors for Chlorinated Hydrocarbons in Water by the Use of Tapered Silver Halide fibers and Tunable Diode Lasers", Applied Spectroscopy, 1995, 1174 to 1177.

8) J. F. Kastner et al.: "Optimizing the Optics for Evanescent Wave Analysis with Laser Diodes (EWALD) for Monitoring Chlorinated Hydrocarbons in Water", SPIE vol. 2783 (1996), 294 to 306.

9) DE 40 38 354 C2

A further material for the optical fibers (preferred to a lesser extent) could be chalcogenic glass.

Most recently, synthetic diamonds can also be produced in the form of suitable fibers. For the present invention, a relatively short, very thin piece of optical fiber material is sufficient. In the case of diamond, the fiber preferentially has, for manufacturing reasons, a quadratic or rectangular cross section. This synthetic diamond material is preferentially produced by layered deposition from the gas phase, in particular, using chemical vapor deposition (CVD). A thin "needle" can be fashioned from the formed layer, as will be described below. The optical properties of diamond in the relevant infrared wavelength region of the light are not as good as those of the above mentioned fiber materials. The transmission is however sufficient for making the measurement. The diamond material has the particular advantage of being corrosion resistant to, among others, salt-containing solutions. Further details can be taken from German patent application 19734617.0 filed on Aug. 9, 1997 entitled "Device for the Investigation of a Sample Substance Using Attenuated Total Internal Reflection", the complete disclosure of which is hereby incorporated by reference.

Germanium and silicon are additional materials suitable for the light guide. These materials, with high purity, have good transmission properties for IR light (for example, Ge lenses are utilized for IR cameras). Since the micro mechanics for processing these materials has been highly developed, the thin needles required within the framework of the invention can be manufactured in an acceptable fashion. Although their high index of refraction creates problems for coupling the light into the needle, the intensity losses associated therewith are acceptable.

Within the framework of the invention, the optical fibers must not, in general, have a round cross section. The expression "fiber" is to be understood as a piece of light guiding material having a length sufficient for insertion through the skin along the required length of the hollow needle (at least approximately 3 mm) and having a cross section which is very small relative to its length. The hollow needles should preferentially have an outer diameter of at most 0.8 mm, and particularly preferred, of at most 0.5 mm or even 0.3 mm. Assuming a wall thickness of 0.05 mm, the associated inside cross section has a diameter of 0.7 mm, 0.5 mm, or 0.2 mm respectively. The cross section of the fiber must be such that it passes through this small lumen of the hollow needle. Should the fiber be non-round in shape, the hollow needle can also have a corresponding non-round cross section.

Additional preferred embodiments, described in more detail with regard to the embodiments shown in the figures, provide for the following features:

The cross section of the optical fiber in the measuring section is not constant, rather varies. There is one or are a plurality of transitions between a larger optical fiber cross section and a smaller optical fiber cross section. In this manner, (as described in a different context in the above mentioned publications) the number of reflections in the optical fiber and therefore the sensitivity of the measurement is increased.

The optical fiber is jacketed within a semi-permeable membrane in such a manner that the interstitial liquid in the measuring section can only penetrate to the surface of the optical fiber through the membrane. The semi-permeable membrane has a cut-off for large molecules having a molecular size in excess of 5,000 Da, preferentially for molecules having a molecular size in excess of 1,000 Da. The cut-off should be as sharp as possible and the permeability rate for smaller molecules should be as high as possible. The membrane leads to an increase in the precision for a given degree of measuring effort. Alternatively, a desired measuring precision can be achieved more easily. Protein deposits on the surface of the light guide and other interfering effects associated with large molecules are avoided. For example, the number of wavelengths required for analysis can be reduced. Moreover, the semi-permeable membrane reduces rejection of the probe penetrating into the skin by the body. As a result, the length of time of use inside the body can be extended. In particular, polysulfone, polyamide, polyethylene, polycarbonate and cellulose can be utilized as a material for the membrane.

The optical fiber is provided in the measurement region with a coating which may serve a plurality of purposes. On the one hand, it can protect the fibers from corrosion. In addition, it can constitute a spacer to prevent direct contact between the optical fiber and a semi-permeable membrane jacket. A material can be chosen for the coating which leads to an enrichment of the analyte at the surface of the optical fiber.

The invention will now be described in more detail on the basis of embodiments schematically shown in the figures.

Figure 1:
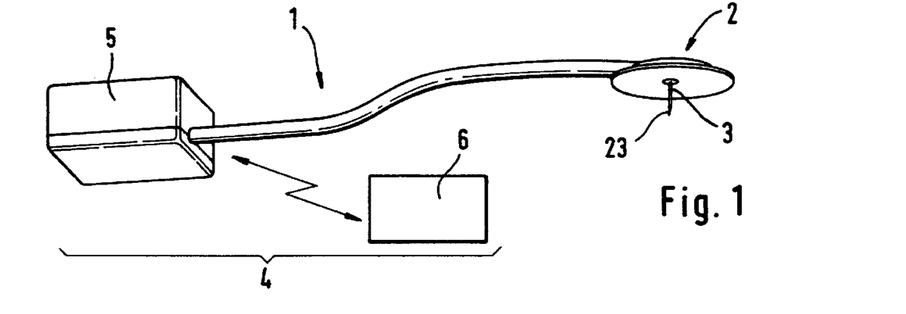
FIG. 1 shows an analysis device in accordance with the invention in perspective view.

The analysis device 1 shown in FIG. 1 consists essentially of a probe head 2 having a measuring probe (piercing probe) 3 which can be pierced through the skin surface and a measurement and analysis unit 4. In the example shown, the measurement and analysis unit 4 has two spatially separated components. An electronics unit 5 can be carried along with the probe head 2 on the body of the patient and preferentially contains only those electronic elements which are necessary to feed the measuring light into the probe 3 and for measuring the modification of the measuring light returning from the probe which characterizes the concentration of the analyte. The resulting measurement signals are stored in the electronics unit 5 and transferred for evaluation, preferentially wireless, to a central evaluation electronics 6 which constitutes the second component of the measurement and evaluation unit 4 and comprises electronic means for receiving the measurement signal and for further processing in the respectively required manner.

Details concerning the function of the measurement and analysis unit 4 as well as the distribution of its tasks between the two components 5 and 6 depend on the individual case. For example, it can be advantageous for the electronics unit 5 to have a sufficient degree of intelligence to extract concentration values of the analyte to be determined and to display them on a screen. The evaluation electronics 6 fulfills longer term duties, in particular, it provides for long-term storage of the measurement data, the display of curves, etc. When the evaluation device is configured for the determination of blood glucose for diabetics, it can e.g. be advantageous to continuously display the blood glucose values on the electronics unit and to trigger an alarm signal, when these values fall below or exceed certain limiting values. In this case, the evaluation electronics may allow to store data for use by the physician and possibly to calculate the dosing of insulin for the therapy.

Figure 2:
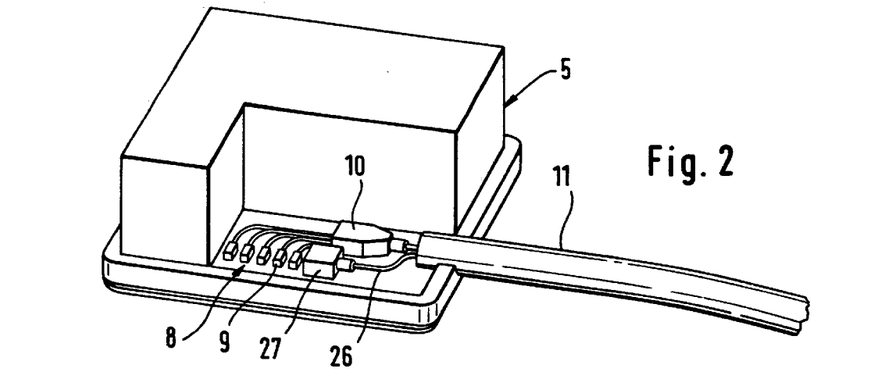
FIG. 2 shows a perspective view of the electronics unit of the device of FIG. 1.
Figure 3:
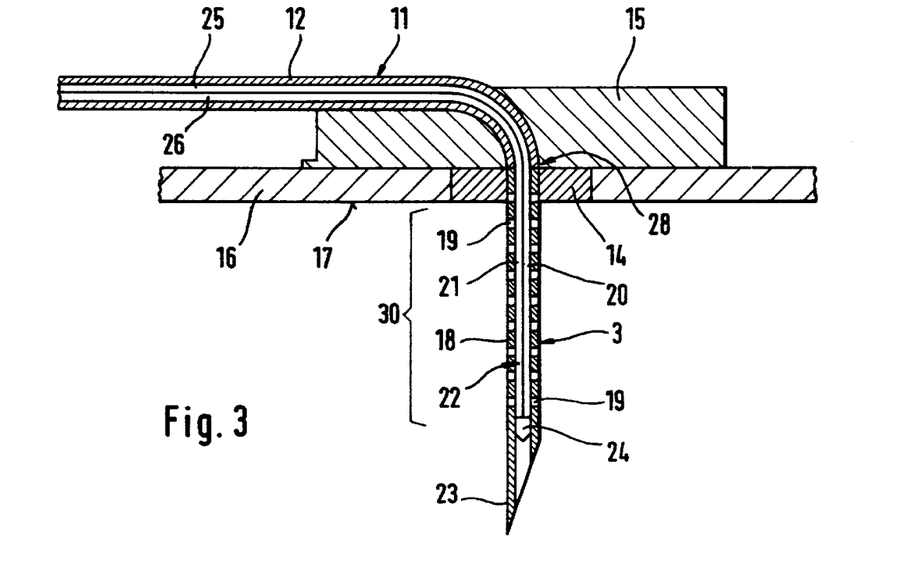
FIG. 3 shows a cross sectional representation of the probe head of the device of FIG. 1.

Details concerning the electronics unit 5 and a measuring probe 2 are shown in FIGS. 2 and 3. The electronics unit 5, shown in FIG. 2 with a removed cover, comprises at least one light source 8 for producing the measuring light. In the example shown, five semiconductor light sources 9 (light emitting diodes or laser diodes) are provided whose light is combined by a beam combiner. The resulting light beam is fed into a fiber optical cable 11 connecting the electronics unit 5 to the probe 2.

The piercing probe 3 is fixed in the probe head 2 by means of two support discs 14 and 15 (FIG. 3). The upper support disc 15 serves both to relieve tensile loads and to guide the fiber optic cable 11. A skin contact disc 16 is provided for mounting to the skin and can e.g. have an adhesive lower side 17 in order to attach the probe 3 to the skin surface. Instead of the perpendicular orientation between the piercing probe 2 and the skin contact disc 16 shown, other configurations are possible wherein the piercing probe 3 penetrates into the skin at an angle of less than 90 degrees, angles between 30 and 60 degrees relative to the surface of the skin being preferred. In this way, a relatively long piercing probe 2 can be used and the penetration depth can nevertheless be kept below a limit desired for physiological reasons.

The piercing probe 3 consists essentially of a hollow needle 18 perforated with holes 19 and made from a material which is physiologically acceptable (for example stainless steel). It contains two parallel fiber lengths or tracks 20 and 21 of an optical fiber 22 and a prismatic reflector 24 disposed proximate the distal end 23 of the hollow needle 18. The reflector 24 is coupled to the distal ends of the fibers 20 and 21 in such a manner that light coupled in via one of the fibers (the inbound fiber track 20) can be reflected back into the other fiber (the return fiber track 21).

In the embodiment shown, two parallel optical fiber tracks run in the fiber optic cable 11 within a flexible jacket 12. The measuring light from the beam combiner 10 is coupled into the first (inbound) fiber optic track 25 of the cable 11 and further guided into the inbound fiber track 20 of the measuring probe 3. Following reflection at reflector 24, the measuring light is guided back through the return fiber track 21 of the measuring probe 3 and through an associated return fiber track 26 of the fiber optic cable 11 and into the electronics unit 5, where it is detected by a detector 27.

In the embodiment shown, the inbound fiber tracks 25 and 20 as well as the return fiber tracks 26 and 21 of the probe 3 and of the fiber optic cable 11 are each designed as a single piece, i.e. they are each made from a continuous fiber of integral fiber material. This is preferred due to ease of manufacture and low intensity losses.

Alternatively, however, the fiber tracks extending in the measuring probe 3 can be made from a material different from that used outside of the measuring probe (in the fiber optic cable 11). In this case the light may be coupled into the respective following fiber track near the proximal end 28 of the hollow needle 18. This is particularly suitable when there are technological problems to produce from the fiber material used for the tracks 20, 21 of light guide fiber 20 running inside the probe fibers having a sufficient length to cover the entire path 25, 20 or 26, 21.

The perforation holes 19 extend through a partial section of the hollow needle 18. The corresponding partial lengths of the optical fiber 22 running in the hollow needle 18 (in the example shown, both fiber tracks 21 and 22) are designated as the measuring section 30. In this measuring section 30, the surface of the optical fiber 22 is, inside the skin tissue and via the perforation holes 19, in contact with the interstitial liquid surrounding the hollow needle 18. In order to allow intensive molecular exchange, the hollow needle 18 is perforated to the highest possible extent. The hole diameter depends mainly on the method of production of the holes and can vary substantially. It should preferentially lie between approximately 1 $\mu$m and approximately 100 $\mu$m.

The holes can advantageously be produced by laser drilling. The fraction of perforation holes in the surface of the hollow needle at the measuring section 30 should be appropriately large. A pore fraction of at least 20% and preferentially at least 50% is currently attempted.

Figure 5:
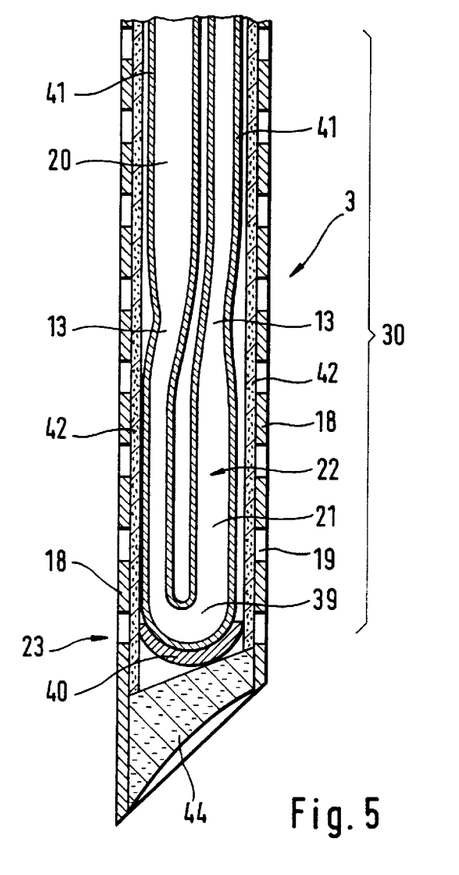
FIG. 5 shows an alternative embodiment of the insertable measuring probe.
Figure 6:
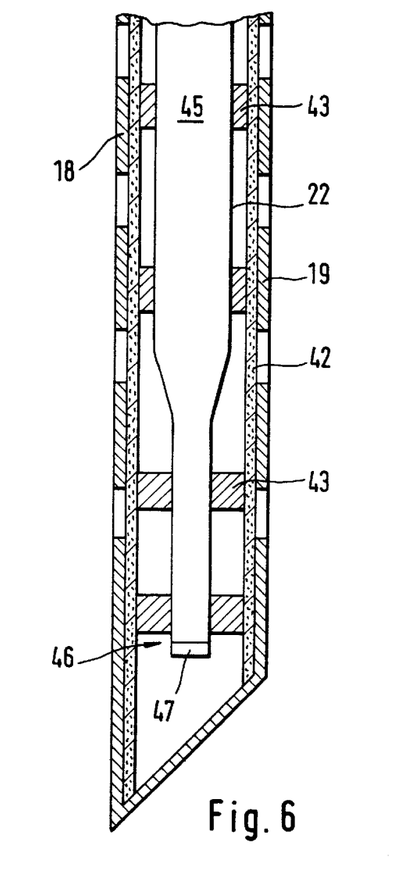
FIG. 6 shows a further alternative embodiment of the insertable measuring probe.

In addition to serving for detection of the analyte, the hollow needle 18 can also be used to subcutaneously administer medication (in particular insulin). In this case, the housing of the electronics unit 5 contains an insulin pump (not shown) and the fiber optic cable 11 contains a tube (not shown) for transporting the medication into the hollow needle 18. The medication flows in the hollow needle 18 past the optical fiber 22 and gains access into the tissue via the perforation holes 19. This causes an interruption of the contact between the interstitial liquid and the surface of the optical fiber, which can be advantageously utilized for zero calibration of the optical measurement. A rinsing solution or a calibration standard solution can also be introduced along the same path. In this embodiment it is favorable that the distal end of the hollow needle is open so that the introduced liquid can exit therefrom. In other embodiments, a hollow needle is preferred which is closed at the distal end (as shown in FIG. 5 and 6). In any event, the distally forward most portion of the optical fiber 22 should be located back from the distal end 23 of the hollow needle 18 so that the sensitive optical fiber 22 is completely surrounded and protected by the hollow needle 18.

Figure 4:
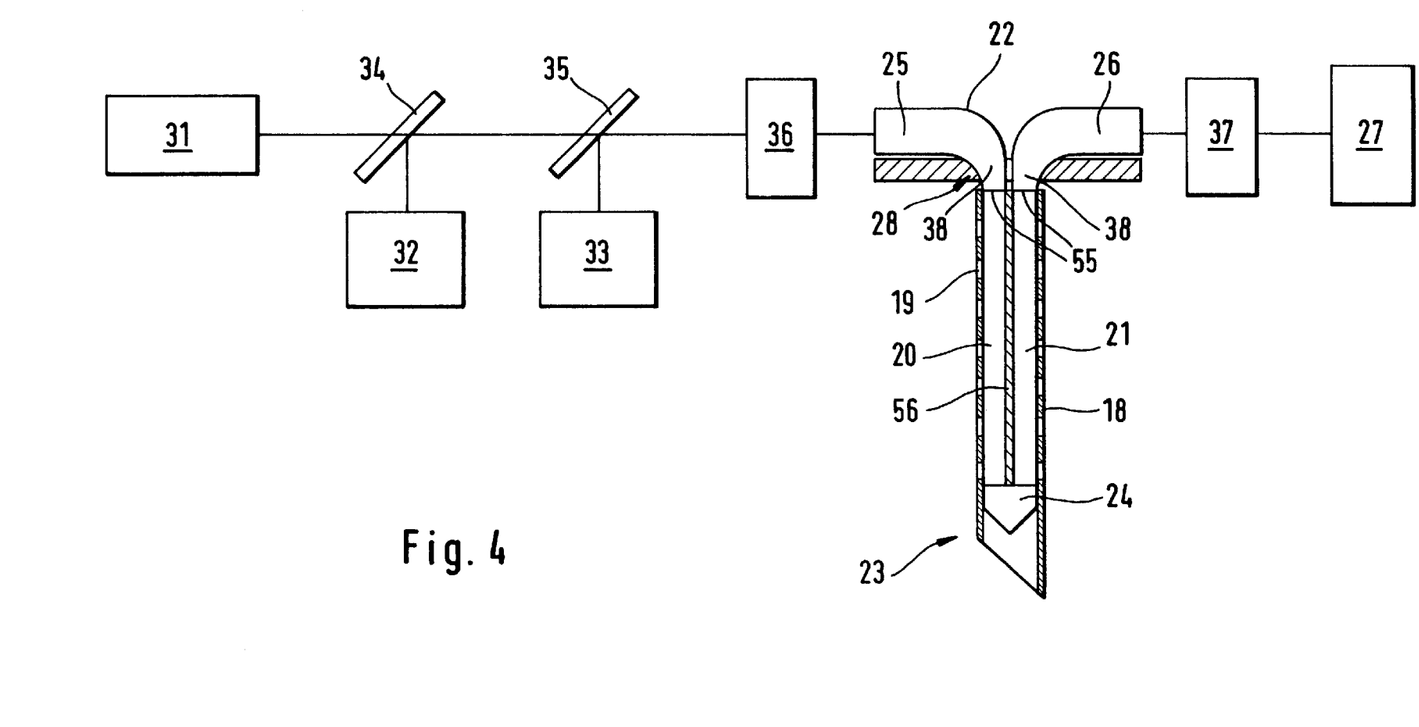
FIG. 4 shows a schematic representation of the irradiation and detection means in a first embodiment of the invention.

A laser light source is preferred for the measuring light, in particular, to facilitate a high optical spectral density and for good focusing onto the end surface of very thin optical fibers. Laser light sources are monochromatic and generally have a fixed, unchangeable wave length. FIG. 4 shows how, in an embodiment of the invention, a spectroscopic measurement can be carried out with a plurality of laser light sources of differing wavelengths.

In the embodiment shown, three different wavelengths are provided, using three lasers 31 through 33. The output of the first laser 31 is oriented directly into the optical axis of the configuration. The light from the two other lasers 32 and 33 is deflected into the same optical axis using semitransparent mirrors 34 and 35. A coupling optics 36 is provided for coupling the light into the inbound fiber tracks 25, 20. A second coupling optics 37 serves for coupling out the measuring light, guided via the return fiber tracks 21, 26, onto the detector 27. The spectral sensitivity of the detector 27 has a sufficient bandwidth to allow detection of all wavelengths of the lasers 31 through 33.

Clearly, measurements at more than three wavelengths can be carried out with a correspondingly increased number of lasers. For measurements in the mid infrared, quantum cascade lasers are preferred.

A particular feature of the embodiment shown in FIG. 4 (compared to that of FIG. 3) is that, before the optical fiber 22 enters into the hollow needle 18, a transition occurs from a thicker fiber track 25 extending in the cable 11 to a fiber track 20 of thinner cross section in the hollow needle 18. A corresponding transition is located on the return path between a thin fiber track 21 in the hollow needle 18 to a thicker fiber track 26 in the cable 11. For reasons of clarity only, FIG. 4 shows the fiber tracks 25 and 26 travelling in opposite directions. It would be generally more advantageous to guide them through a single cable 11.

The tapering 38 of the optical fibers 22 shown in FIG. 4 prior to entrance into the hollow needle 18 permits a relatively thick optical fiber to be used in the fiber optic cable, having better mechanical stability and lower optical losses. It has turned out that an optical fiber in the hollow needle 18 having a very small cross section (corresponding to a diameter of less than 0.2 mm) reduces patient discomfort and improves measurement sensitivity.

In the embodiment of FIG. 4 having the taper 38, it is advantageous, as already mentioned, when the fiber tracks 20, 21 are separate from the fiber tracks 25, 26 and possibly made from a different material. The coupling-over locations near the proximal end 28 are designated in FIG. 4 with reference symbol 55. The fiber tracks 20, 21 in the hollow needle 18 are separated by a metal strip 56, reflecting on both sides. This prevents optical cross-talk. The semicircular shaped fiber tracks 20, 21, preferred for this design, may be initially mounted to the separation strip 56 when assembling the sensor and be introduced together into the hollow needle.

FIG. 5 shows a piercing probe 3 having, as in FIG. 3, two optical fiber tracks 20, 21 running parallel to each other in the hollow needle 18, wherein the light is transported through an inbound fiber track 20 towards the distal end 23 of the hollow needle 18. As in FIG. 3, a deflection into the opposite direction is effected proximate the distal end 23 of the hollow needle 18 and the light is guided out of the hollow needle 18 through the return fiber track 21. The embodiment shown in FIG. 5 differs from the embodiment of FIG. 3 with regard to the following features.

The deflection of the light proximate the distal end 23 of the hollow needle 18 is effected here with a narrow deflection loop 39 in a continuous optical fiber 22. In contrast to reference 4), the region of the deflection loop 39 is not used for measurement. On the contrary, a reflecting cap 40 makes sure that the light is deflected with as low reflection losses as possible and does not couple out.

The optical fiber tracks 20 and 21 each have a tapered location 13 at which the cross section of the optical fiber is transformed from a larger value to a smaller value in order to increase, as described, the number of reflections and the sensitivity of the measurement. Instead of the relatively rapid transition shown, a slow tapering over the entire measuring section 30 can also be advantageous. It is also possible to provide for a plurality of regions in each of the optical fiber tracks extending in the measuring section 30 having varying optical fiber cross section.

The optical fiber 22 in FIG. 5 has a coating 41 which on the one hand does not interfere with the measurement but, on the other hand, fulfills one or more of the above discussed purposes. The following types of coating materials may be used.

The coating may be made from a very thin (e.g. evaporated) metal layer. The metal (preferentially a precious metal, particularly silver) protects the optical fiber 22 from corrosion. In addition, it is suitable as a spacer for a membrane 42 surrounding the optical fiber 22. Since even a very thin metallic layer substantially interferes with the exit of evanescent waves, it should be interrupted for the case of ATR measurements so that a substantial fraction of the surface has direct contact between the interstitial liquid and the optical fiber. In conjunction with a thin metal layer, other interaction mechanisms between the light transported in the optical fiber 22 and the interstitial liquid are possible, namely surface plasmons.

Alternatively, it can be advantageous to provide the optical fiber 22 (at least at the measuring location 30) with a coating made from a polymer. The polymer is chosen substantially not to absorb in the spectral region of the measuring light. The polymer coating also serves to protect the fibers from corrosion and is a spacer to prevent direct contact between the membrane jacket 42 and the optical fiber 22. In particular the following polymer materials, are currently considered suitable: polytetrafluor ethylene, polyisobutylene, polycarbonate.

A polymer coating which has analyte enriching properties is particularly preferred. This is described in references 8) and 9) in connection with non-medical ATR measurements. For each desired analyte a coating having these properties must be found experimentally.

Another special feature of the embodiment shown in FIG. 5 is a membrane 42 jacketing the optical fiber 22 in the measuring section 30. As already mentioned, the membrane prevents substances of high molecular weight from reaching the surface of the optical fiber 22 thus allowing better measuring precision with a reduced degree of measurement difficulty. Clearly, suitable sealing means must be used to prevent an amount of interstitial liquid which would interfere with the measurement from penetrating to the optical fibers 22 via remaining gaps. In the example shown, the hollow needle 18 is e.g. sealed by a drop 44 of epoxy resin which also seals the lower portion of the membrane 42.

Suitable membrane materials having the desired mechanical, chemical and dialysis properties for the current application are known in the art of so-called micro-dialysis methods. Reference is hereby made, in particular, to 10) U.S. Pat. No. 4,694,832 and the references cited therein.

Particularly suitable membrane materials have already been mentioned above.

Within the context of the invention, it has been determined that the advantageous effects of a membrane 42 jacketing the optical fibers 22 can be negatively influenced if the membrane directly touches the optical fiber 22. Transport of the measuring light in the optical fiber 22 can thereby be disrupted in a manner which is disadvantageous to the precision of the measurement. It is therefore particularly preferred within the context of the present invention for the membrane to be substantially separated from the outer surface of the optical fiber 22. In this context "substantially separated" means that possible remaining contact surfaces between the membrane and the outer surface of the optical fiber 22 are sufficiently small that the precision of the measurement is not disturbed to a significant extent. The contact surface should, in any event, be less than 50%, preferentially less than 20% and particularly preferentially less than 10% of the surface of the optical fiber 22 in the measuring section 30. The size of the gap between the optical fiber 22 and the membrane (where they are separated) is important for the measurement precision. It should preferentially be at least two times and preferentially at least three times the wavelength of the measuring light. The maximum separation is given by the dimensions of the components and by the need for a sufficiently rapid diffusion exchange. In practical applications, it is less than 100 $\mu$m. A coating 41 on the optical fiber 22 may be provided as a spacer (see FIG. 5). No separation between the membrane 42 and the optical fiber 22 is necessary if the membrane does not have interfering optical absorption in the spectral range of the measuring light.

FIG. 6 shows an alternative possibility for producing a separation between the optical fiber 22 and the membrane 42. Here the membrane 42 coats the inner surface of the hollow needle 18. The optical fiber 22 is fixed in the hollow needle 18 using spacer rings 43 preferentially made from a material which does not absorb or absorbs only weakly in the infrared region. Alternatively, (however currently not particularly preferred) the membrane could be disposed on the outer surface of the hollow needle 18. Evidently, in such an embodiment the separation from the surface of the optic fiber 22 is provided by the wall of the hollow needle 18.

Another particular feature of the embodiment shown in FIG. 6, is that only one optical fiber track 45 extends in the measuring section 30 of the hollow-needle 18, which is closed at its lower end. A mirror 47 made e.g. from gold is disposed at the distal end 46 to reflect the light back along the same optical fiber track 45.

Figure 7:
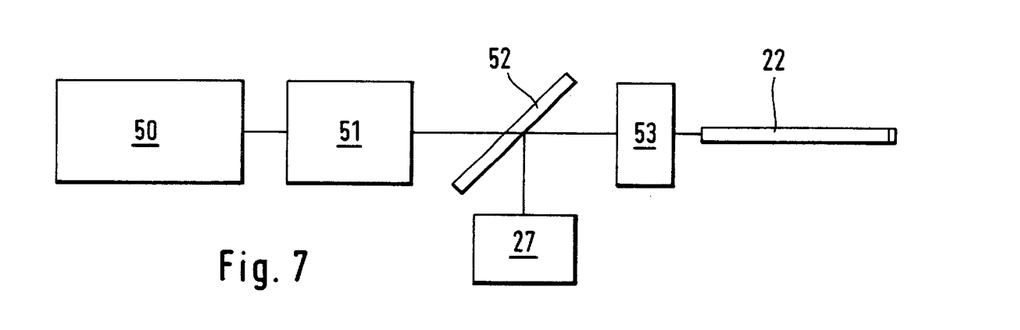
FIG. 7 shows a schematic representation of optical irradiation and detection means suitable for the measuring probe of FIG. 6.

In the embodiment shown in FIG. 6, the measuring light must be suitably coupled into and out of the single optical fiber track 45. One way of doing this is schematically shown in FIG. 7. A band-pass spectral filter 51 is used to select the desired wavelength region from the light emanating from a broad-band emitting light source 50. The resulting light passes through a beam splitter 52 and coupling optics 53 into the optical fiber 22. After reflection at the reflector 47, the light passes through the coupling optics 53 and is incident on the beam splitter 52 to be reflected onto the detector 27. Instead of the broad-band light source 50, a configuration having a plurality of lasers (as shown in FIG. 4) can also be used.

Figure 8:
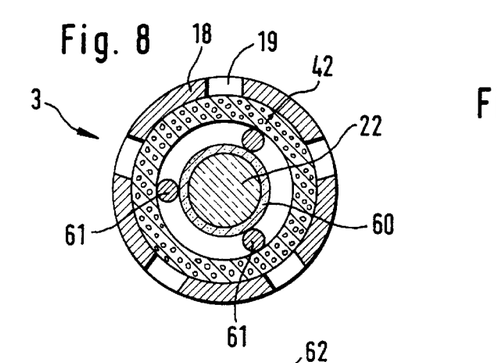
FIG. 8 shows a cross section through a measuring probe similar to FIG. 6.

FIG. 8 shows a cross section through a piercing probe 3 having a design similar to that of FIG. 6, however with an optical fiber 22 having a coating 60 made from diamond or diamond like carbon (DLC). The coating preferentially surrounds the optical fiber completely along the entire length of the measuring section 30. A diamond coating of this kind provides effective protection for the material of the optical fiber 22 against corrosion. It is also advantageous from a point of view of bio-compatibility. It even permits use of toxic substances for the light guide such as e.g. a TlJ-TlBr mixture.

The diamond coating 60 is preferentially made by deposition from the gas phase, a low temperature CVD process being particularly preferred.

Coating a light guide with a diamond layer is disclosed in WO 97/06426. In accordance with this reference, the diamond layer should always have an index of refraction which is smaller than that of the light guide. This is to assure, as with conventional cladding of optical fibers, that the conditions of internal reflection necessary for light transport in the optical fiber are maintained. In contrast to this prior art, the present invention prefers a coating preferably but not exclusively made from diamond whose index of refraction is larger or at least as large as that of the optical fiber. If this layer is extremely thin, total internal reflection is not impaired. On the contrary, a very effective interaction between the light transported in the optical fiber and the liquid surrounding the coating is effected via the surrounding evanescent field. This is particularly true in an embodiment having a light guide made from a silver halide, coated with a diamond layer.

A further possibility for separating the optical fiber 22 from the membrane 42, shown in FIG. 8, is the use of a metal wire (preferentially made from gold) extending in the longitudinal direction of the hollow needle.

Figure 9:
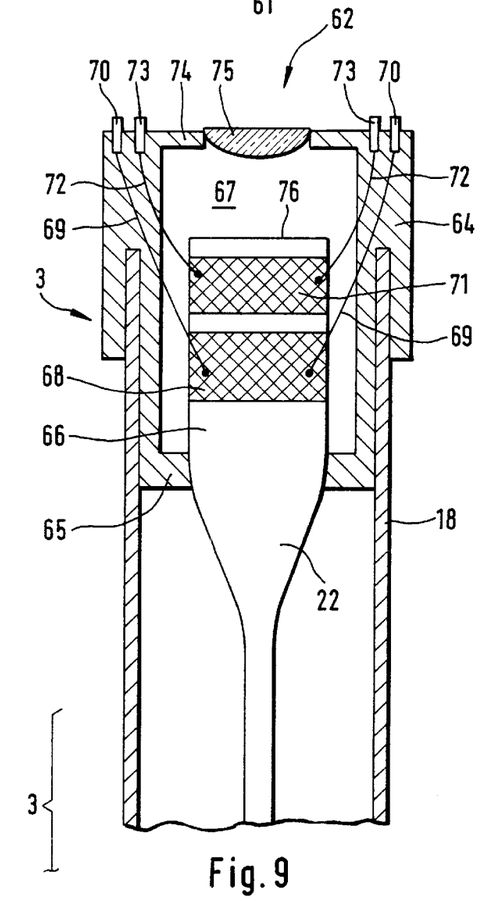
FIG. 9 shows a longitudinal section through the upper (proximal) portion of a measuring probe similar to FIG. 6.

FIG. 9 shows an advantageous embodiment of the proximal end 62 of a measuring probe 3. In the example shown, a separable (plugable) connection is provided between the fiber optic cable 11 introducing the light and the track of optical fiber 22 extending in the hollow needle. A locking member, designated with reference symbol 64, can be plugged onto the proximal end 66 of the hollow needle 18. This end can also be designated as the coupling end. The locking member 64 has a support collar 65 which surrounds the optical fiber 22 tightly and in a sealing fashion. To this end the locking member 64 is advantageously made from a sufficiently elastic material. The proximal thickened end 66 of the optical fiber 22 projects into a coupling chamber 67 provided in the locking member 64 which is sufficiently large as to have a free space between its bordering walls and the section of the optical fiber located therein. A heating film 68 made e.g. from a nickel-chrome alloy is disposed on that portion of the optical fiber 22 penetrating into the coupling chamber 67 and is connected to heating connections 70 via heating leads 69 for feeding in electrical power.

The portion of the optical fiber 22 penetrating into the coupling chamber 67 also has a temperature measuring film 71 e.g. in the form of a Pt-100 precision resistor layer connected, via measuring leads 72, to measuring connections 73. The upper end surface of the locking member 64 has a mounting collar 74 in which a coupling lens 75 is disposed for coupling light into and out of the proximal end surface 76 of the optical fiber 22.

This embodiment is particularly advantageous when the optical fiber 22 is made from diamond. Although the heating film 68 and the temperature measuring film 71 are relative far removed from the measuring section 30 at the proximal end of the optical fiber 22 in the locking member 64, and despite the very narrow cross section of the optical fiber 22 a proper control of the temperature in the measuring section of the optical fiber 22 is possible due to the very high heat conductivity of diamond. The precise temperature measurement using the temperature measuring film 71 or some other temperature measuring element can be advantageously used for compensation of temperature dependencies when evaluating the spectral measurements.

An optical fiber 22 having the desired small size can preferentially be fashioned out of a thin diamond layer deposited from the gas phase. Manufacture of diamond layers by means of the CVD method is known in the art and is described e.g. within the context of an enzyme glucose sensor in the following publication:

C. E. Troupe et al. "Diamond-based Glucose Sensors" in Diamond and Related Materials, 1968, 575 to 580.

In order to fashion a thin needle-shaped, self-supporting optical fiber as shown in FIG. 9 from a layer produced on a substrate using the CVD method, the surface thereof is advantageously initially polished smooth and the desired sideward shape is then cut-out using a laser. The substrate used for the CVD process is then removed by etching. An etching method should be used which delivers as smooth a surface as possible.

Figure 10:
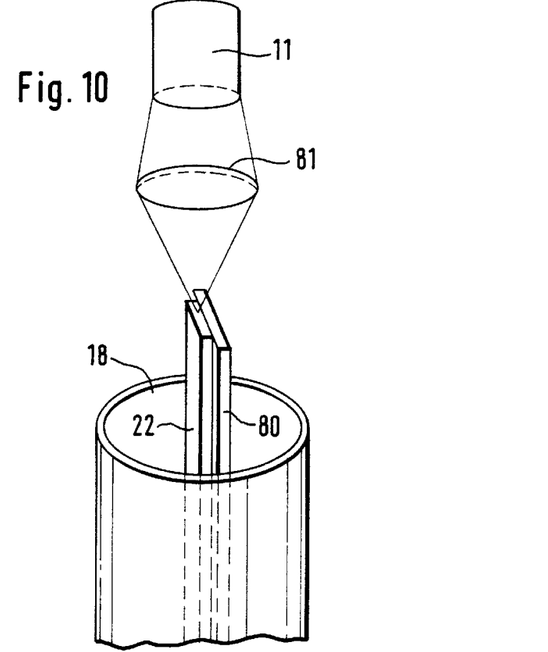
FIG. 10 shows a schematic perspective representation of a portion of an additional, modified embodiment of a measuring probe.

When using an optical fiber material produced as a thin layer on a substrate, in particular diamond, silicon and germanium, the optical fiber can be advantageously integrated together with the substrate into the hollow needle. A highly schematic representation of this configuration is shown in FIG. 10. An optical fiber 22 having a rectangular cross section is disposed on a substrate 80 also having a rectangular cross section. A free beam coupling-in optics 81 is provided for coupling-in the light from a fiber optic cable 11 into its end face. It can, as shown in FIG. 9, be embodied as a coupling lens 75 in a locking member 64.

The hollow needle 18 is shown in exaggeratedly large scale in FIG. 10. Due to the extremely small dimensions which are desired within the framework of the invention for the hollow needle 18 it would initially appear to be difficult to accommodate both an optical fiber and an integrated substrate layer in the very small lumen of diameter e.g. less than 0.5 mm. However, a CVD optical fiber layer on a stable substrate with high tensile strength can advantageously provide high stability for small cross sections of the optical fiber layer 22. Semiconductor technology has developed very reliable methods for micro-mechanical processing of such layers so that it is possible to produce the layered packet 22, 80 having the desired extremely small dimensions and good strength properties.

Of the materials normally used for the processing of CVD diamond layers, molybdenum is particularly suitable within the framework of the present invention, with its surface being processed in such a fashion that it is mirror smooth. Silicon, often used for other applications, is however not suitable for a diamond optical fiber, since the index of refraction of a transparent substrate material must be less than that of the optical fiber material. In general, possible substrate materials include those having an index of refraction which is less than that of the material in the optical fiber and which exhibit as low a degree of optical attenuation as possible, e.g. metal, quartz, sapphire or ceramics.

Figure 11:
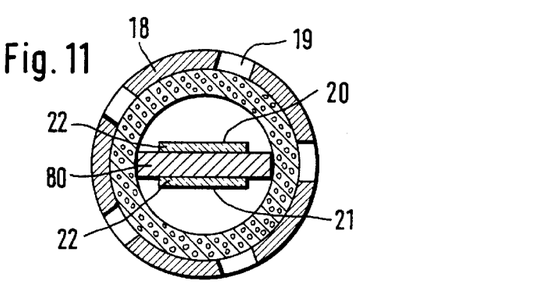
FIG. 11 shows a cross section through a first variation similar to the embodiment of FIG. 10.
Figure 12:
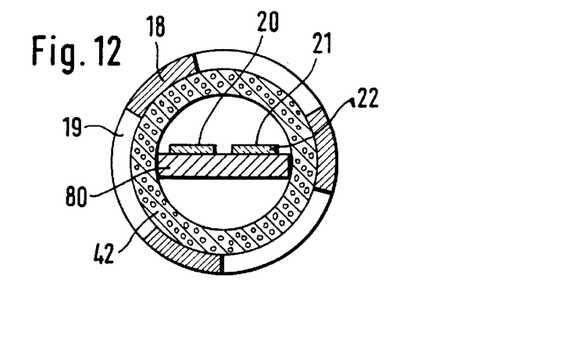
FIG. 12 shows a cross section through a second variation similar to the embodiment of FIG. 10.

FIGS. 11 and 12 show cross sections of varying configurations for the optical fiber relative to the substrate 80. In the configuration shown in FIG. 11, the substrate 80 is provided on both sides with optical fibers 22 having rectangular cross sections, constituting, similar to the embodiment according to FIG. 1, an inbound fiber track 20 and a return fiber track 21. Deflection at the distal end can e.g. be effected using a prismatic reflector similar to FIGS. 3 and 4.

In the variation shown in FIG. 12, both the inbound fiber track 20 as well as the return fiber track 21 are located on one side of the substrate. In this case, deflection on the distal end is advantageously effected by a U-shaping of the optical fiber 22, similar to FIG. 5. As in FIGS. 5 and 6, both FIG. 11 and FIG. 12 show a membrane on the inside of the hollow needle 18. A comparison between FIGS. 11 and 12 shows that the perforation holes 19 of the hollow needle 18 can have differing sizes. Their shapes can also be different. In addition to a round shape, an elongated slot-like shape is also possible.

As can be seen in FIG. 11, the desired separation between the optical fiber 22 and the membrane 42 in these embodiments is effected by a suitable cross sectional shaping of the substrate 80.

The use of a thin layer material disposed on a substrate creates particular problems with regard to the coupling-in of the light from the electronics unit (as in FIGS. 1 and 2) via a fiber optic cable. FIGS. 13 through 18 show differing embodiments for this coupling, wherein the inbound fiber track of a fiber optic cable for introducing the light (see FIG. 3) is designated with 25 and the subsequent introductory fiber track of the measuring probe is designated with 20, in each case. Clearly, the same principles can be used for coupling the light between corresponding return fiber tracks 26, 21 or an optical fiber 22 can be used which (as in FIG. 10) simultaneously serves for introducing and returning the light.

Figure 13:
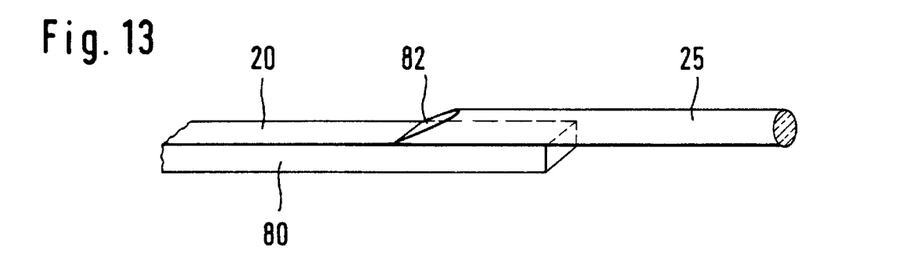
FIG. 13 shows a perspective partial view of a first embodiment of a configuration for coupling light into and out of an optical fiber disposed on a substrate.

In the embodiment shown in FIG. 13, the fiber track 25 of the introductory fiber optic cable is coupled to the rectangular cross section of the optical fiber 22 by pressing on its bordering edges. This method is suitable in cases with which one of the optical fibers which are to be coupled to each other (in this case the fiber track 25) has a lower hardness than the other fiber (in this case 20). This is particularly the case when one of the optical fibers 20 is made from diamond and the other optical fiber 25 is made from a comparatively soft material e.g. a silver halide. Particularly well suited is $AgBr_xC_{1-x}$ with x=0.75. The pressed-on fiber 25 has a bevel 82 at one end to effect a relatively continuous radiative transition between the fibers 25 and 20. The embodiment facilitates a simple, alignment-free optical coupling.

Figure 14:
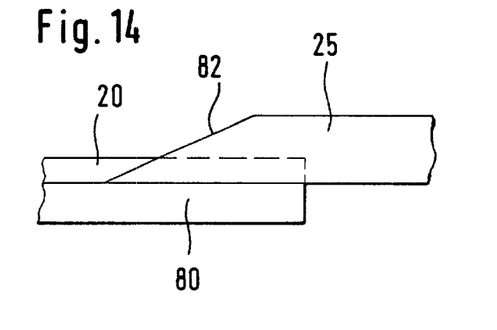
FIG. 14 shows a side view of a variant of the embodiment of FIG. 13.
Figure 15:
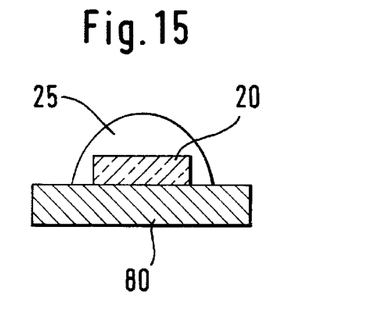
FIG. 15 shows a front view of FIG. 14.

FIG. 14 shows a side view and FIG. 15 a front view of an embodiment which is largely the same as that in accordance with FIG. 13, however the optical fiber 25 is pressed onto the optical fiber 20 through contact with the substrate 80 so that the fiber 25 completely surrounds the fiber 20 on one end. This facilitates mass production.

The press coupling shown in FIGS. 13 through 15 for connecting the light guides is, in principle, also applicable to cases in which the fiber track extending in the hollow needle is not disposed on a substrate, but extends in a self-supporting fashion within the hollow needle 18. For example, a light guide in the form of a diamond needle can be pressed into a silver halide fiber.

Figure 16:
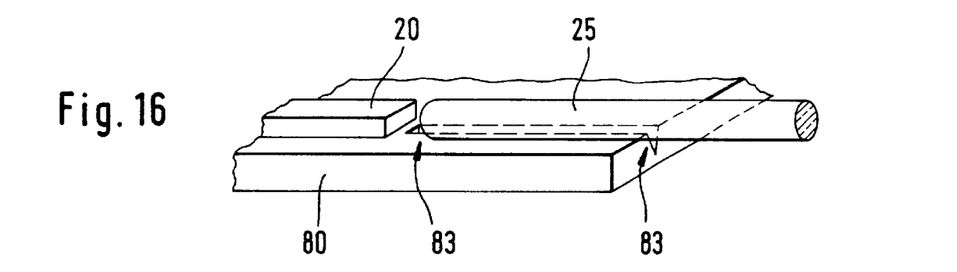
FIG. 16 shows a perspective partial view of a third variant of the embodiment of FIG. 13.

In the embodiment shown in FIG. 16, the optical coupling is realized without direct contact between the fibers 25 and 20. The end of the fiber 25 shown is positioned into a groove provided for in the substrate 80, designated as a positioning trough 83. It serves to position the fiber 25 precisely in front of the oppositely lying end of the fiber 20, fixed to the substrate 80. A gap for free traveling of the light beam is provided between the oppositely positioned ends of fibers 20 and 25, the end of the fiber 25 facing the fiber being rounded in order to effect a focusing lens effect.

Figure 17:
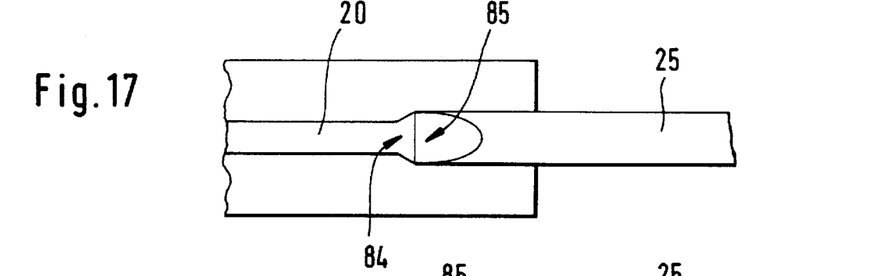
FIG. 17 shows a plan view of a fourth variant of the embodiment of FIG. 13.
Figure 18:
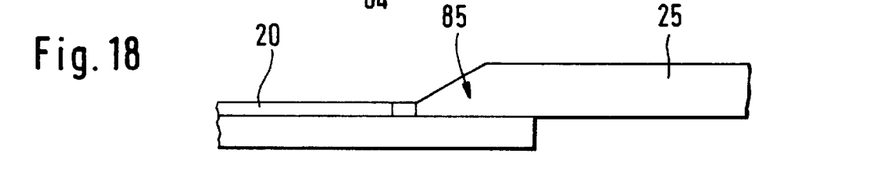
FIG. 18 shows a side view of FIG. 17.

FIGS. 17 and 18 show plan and side views respectively of an embodiment with which the fiber track 20 extending in the probe has an end section 84 widened in a transverse direction. A fiber optic cable for introducing light is adjoined to its end face with cross section matching at a tapered transition 85. By having a smooth cross section this embodiment effects as good an optical transition as possible at the transition position.

What is claimed is:

1. Analysis device for determining an analyte in vivo through skin in the body of a patient comprising a measuring probe having a hollow needle adapted to be pierced into the skin and including a wall being permeable along a partial section of its length which is adapted for penetration into the skin, said permeable partial section defining a measuring section, an optical fiber by which light coupled from a light source into the optical fiber is passed into the hollow needle and thus into the body when the measuring probe is pierced into the skin, wherein the light transported through the optical fiber is modified in the measuring probe by direct reagent-free interaction with interstitial liquid within the body, said modification being characteristic of the presence of the analyte and a measuring and evaluation unit to measure the modification and to derive, on the basis of the modification, information concerning the presence of the analyte in the body, wherein said optical fiber includes a measuring section that extends in at least a part of the measuring section of the hollow needle, said light is modified by interaction with interstitial liquid surrounding said measuring section of said optical fiber in said measuring section of said hollow needle, said interstitial liquid penetrating through said wall of said hollow needle to said measuring section of said optical fiber and the modification of the light characteristic of the presence of the analyte results from an interaction with the interstitial liquid in the treasuring section.

2. Analysis device according to claim 1, characterized in that the cross section of the optical fiber varies along the measuring section.

3. Analysis device according to claim 1, characterized in that only one optical fiber track runs inside the hollow needle in the measuring section, the distal end of the fiber track being provided with a mirror which reflects the light back along the same optical fiber track.

4. Analysis device according to claim 1, characterized in that two parallel optical fiber tracks extend in the hollow needle in the measuring section, wherein the light is transported through the one optical fiber track towards the distal end of the hollow needle and is deflected at the distal end of the hollow needle to return through the other optical fiber track.

5. Analysis device according to claim 4, characterized in that a prismatic reflector is arranged at the distal end of the hollow needle to deflect the light.

6. Analysis device according to claim 1, characterized in that the optical fiber is surrounded, at least in the measuring section, by a coating.

7. Analysis device according to claim 6, characterized in that the coating is metallic.

8. Analysis device according to claim 6, characterized in that the coating is a polymer.

9. Analysis device according to claim 6, characterized in that the coating consists essentially of synthetic diamond including diamond like carbon (DLC).

10. Analysis device according to claim 6, characterized in that the coating has an index of refraction which is at least as large as that of the optical fiber.

11. Analysis device according to claim 1, characterized in that the measuring section of the optical fiber is jacketed by a semi-permeable membrane such that the interstitial liquid in the measuring section only gains access to a surface of the optical fiber through the membrane.

12. Analysis device according to claim 11, characterized in that the membrane is arranged within the hollow needle.

13. Analysis device according to claim 11, characterized in that the membrane is essentially separated from the outer surface of the optical fiber.

14. Analysis device according to claim 13, characterized in that the separation is effected by a coating on the optical fiber.

15. Analysis device according to claim 13, characterized in that the separation is effected by a substrate having a cross sectional dimension projecting past the dimension of the optical fiber.

16. Analysis device according to claim 11, characterized in that the membrane is based on polycarbonate.

17. Analysis device according to claim 1, characterized in that the interaction of the light transported in the optical fiber with the interstitial liquid is due to the penetration of an evanescent field into the interstitial liquid.

18. Analysis device according to claim 1, characterized in that the light source comprises at least one quantum cascade laser.

19. Analysis device according to claim 1, characterized in that the material of the optical fiber is selected from the group consisting of silver halide, chalcogenic glass, synthetic diamond, diamond-like carbon, silicon, and germanium.

20. Analysis device according to claim 1, characterized in that the optical fiber is fashioned from a layer produced by deposition from a gas phase onto a substrate.

21. Analysis device according to claim 20, characterized in that the optical fiber is integrated together with the substrate into the hollow needle.

22. Analysis device according to claim 1, characterized in that a light guide fiber, having a hardness which is less than that of the material from which the optical fiber is made, is joined to the optical fiber by pressing.

23. Analysis device according to claim 1, characterized in that a temperature measuring element is disposed on the optical fiber near a proximal end of the hollow needle.

24. Analysis device for determining an analyte in vivo through skin in the body of a patient comprising a measuring probe having a hollow needle adapted to be pierced into the skin and including a wall being permeable along a partial section of its length which is adapted for penetration into the skin and serves as a measuring section and with an optical fiber which runs inside the hollow needle and by which light coupled from a light source into the optical fiber is passed into the hollow needle and thus into the body when the measuring probe is pierced into the skin, wherein interstitial liquid penetrates through the wall of the hollow needle into a measuring section of the optical fiber in the hollow needle, and wherein the light transported through the optical fiber is modified in the measuring probe by direct reagent free interaction with the interstitial liquid surrounding the optical fiber within the body, said modification being characteristic of the presence of the analyte and a measuring and evaluation unit to measure the modification and to derive, on the basis of the modification, information concerning the presence of the analyte in the body, and wherein the modification of the light characteristic of the presence of the analyte results from an interaction with the interstitial liquid in the measuring section, wherein the wavelength of the light from the light source is between 7 $\mu$m and 13 $\mu$m.

25. Analysis device for determining an analyte in vivo through skin in the body of a patient comprising a measuring probe having a hollow needle adapted to be pierced into the skin and including a wall being permeable along a partial section of its length which is adapted for penetration into the skin and serves as a measuring section and with an optical fiber which runs inside the hollow needle and by which light coupled from a light source into the optical fiber is passed into the hollow needle and thus into the body when the measuring probe is pierced into the skin, wherein interstitial liquid penetrates through the wall of the hollow needle into a measuring section of the optical fiber in the hollow needle, and wherein the light transported through the optical fiber is modified in the measuring probe by direct reagent free interaction with the interstitial liquid surrounding the optical fiber within the body, said modification being characteristic of the presence of the analyte and a measuring and evaluation unit to measure the modification and to derive, on the basis of the modification, information concerning the presence of the analyte in the body, and wherein the modification of the light characteristic of the presence of the analyte results from an interaction with the interstitial liquid in the measuring section, wherein a heating element and a temperature measuring element are disposed on the optical fiber near a proximal end of the hollow needle.

26. Analysis device for determining an analyte in vivo through skin in the body of a patient comprising a measuring probe having a hollow needle adapted to be pierced into the skin and including a wall being permeable along a partial section of its length which is adapted for penetration into the skin and serves as a measuring section and with an optical fiber which runs inside the hollow needle and by which light coupled from a light source into the optical fiber is passed into the hollow needle and thus into the body when the measuring probe is pierced into the skin, wherein interstitial liquid penetrates through the wall of the hollow needle into a measuring section of the optical fiber in the hollow needle, and wherein the light transported through the optical fiber is modified in the measuring probe by direct reagent free interaction with the interstitial liquid surrounding the optical fiber within the body, said modification being characteristic of the presence of the analyte and a measuring and evaluation unit to measure the modification and to derive, on the basis of the modification, information concerning the presence of the analyte in the body, and wherein the modification of the light characteristic of the presence of the analyte results from an interaction with the interstitial liquid in the measuring section, wherein the measuring section of the optical fiber is jacketed by a semi-permeable membrane such that the interstitial liquid in the measuring section only gains access to a surface of the optical fiber through the membrane, the membrane is essentially separated from the surface of the optical fiber, and the separation is effected by a metallic wire travelling in the longitudinal direction within the hollow needle between the optical fiber and the membrane.

27. Analysis device for determining an analyte in vivo in the body of a patient, the device comprising:

a measuring probe having a hollow needle having a length, a partial section of the length being adapted for penetration into the body and in which a wall of the hollow needle is permeable to interstitial liquid surrounding the hollow needle within the body, said partial section defining a measuring section of said hollow needle and an optical fiber including a measuring section that extends inside the hollow needle in the measuring section thereof and by which light is passed, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte and a measuring and evaluation unit to measure the modification and to derive, on the basis of the modification, information concerning the presence of the analyte in the body.

28. The device of claim 27, wherein the wavelength of the light is between 7 $\mu$m and 13 $\mu$m.

29. The device of claim 27 wherein the cross section of the optical fiber varies along the measuring section.

30. The device of claim 27 wherein only one optical fiber track runs inside the hollow needle in the measuring section, a distal end of the fiber track being provided with a mirror which reflects the light back along the same optical fiber track.

31. The device of claim 27 wherein two parallel optical fiber tracks extend in the hollow needle in the measuring section, wherein the light is transported through one optical fiber track towards a distal end of the hollow needle and is deflected at the distal end of the hollow needle to return through the other optical fiber track.

32. The device of claim 31 wherein a prismatic reflector is arranged at the distal end of the hollow needle to deflect the light.

33. The device of claim 27 wherein the optical fiber is surrounded, at least in the measuring section, by a coating.

34. The device of claim 33 wherein the coating is metallic.

35. The device of claim 33 wherein the coating is a polymer.

36. The device of claim 33 wherein the coating consists essentially of synthetic diamond including diamond like carbon.

37. The device of claim 33 wherein the coating has an index of refraction which is at least as large as that of the optical fiber.

38. The device of claim 27 wherein the measuring section of the optical fiber is jacketed by a semi-permeable membrane such that the interstitial liquid in the measuring section only gains access to a surface of the optical fiber through the membrane.

39. The device of claim 38 wherein the membrane is arranged within the hollow needle.

40. The device of claim 38 wherein the membrane is essentially separated from the surface of the optical fiber.

41. The device of claim 40 wherein the separation is effected by a substrate having a cross sectional dimension projecting past the dimension of the optical fiber.

42. The device of claim 40 wherein the separation is effected by a coating on the optical fiber.

43. The device of claim 38 wherein the membrane is based on polycarbonate.

44. The device of claim 27 wherein the interaction of the light transported in the optical fiber with the interstitial liquid is due to a penetration of an evanescent field into the interstitial liquid.

45. The device of claim 27 wherein the light is coupled in from a light source that comprises at least one quantum cascade laser.

46. The device of claim 27 wherein the material of the optical fiber is selected from the group consisting of silver halide, chalcogenic glass, synthetic diamond, diamond-like carbon, silicon, and germanium.

47. The device of claim 27 wherein the optical fiber is fashioned from a layer produced by deposition from a gas phase onto a substrate.

48. The device of claim 47 wherein the optical fiber is integrated together with the substrate into the hollow needle.

49. The device of claim 27 wherein a light guide fiber, having a hardness which is less than that of the material from which the optical fiber is made, is joined to the optical fiber by pressing.

50. The device of claim 27 wherein a temperature measuring element is disposed on the optical fiber near a proximal end of the hollow needle.

51. Analysis device for determining an analyte in vivo in the body of a patient, the device comprising:

a measuring probe having a hollow needle with a measuring section having a length, a partial section of the length being adapted for penetration into the body and in which a wall of the hollow needle is permeable to interstitial liquid surrounding the hollow needle within the body and an optical fiber including a measuring section that extends inside the hollow needle in the measuring section thereof and by which light is passed, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte, a measuring and evaluation unit to measure the modification and to derive, on the basis of the modification, information concerning the presence of the analyte in the body, and a heating element and a temperature measuring element disposed on the optical fiber near a proximal end of the hollow needle.

52. Analysis device for determining an analyte in vivo in the body of a patient, the device comprising:

a measuring probe having a hollow needle with a measuring section having a length, a partial section of the length being adapted for penetration into the body and in which a wall of the hollow needle is permeable to interstitial liquid surrounding the hollow needle within the body and an optical fiber including a measuring section that extends inside the hollow needle in the measuring section thereof and by which light is passed, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte, and a measuring and evaluation unit to measure the modification and to derive, on the basis of the modification, information concerning the presence of the analyte in the body, wherein the measuring section of the optical fiber is jacketed by a semi-permeable membrane such that the interstitial liquid in the measuring section only gains access to a surface of the optical fiber through the membrane, the membrane is essentially separated from the surface of the optical fiber, and the separation is effected by a metallic wire travelling in the longitudinal direction within the hollow needle between the optical fiber and the membrane.

53. Analysis device for determining an analyte in vivo in the body of a patient, the device comprising:

a measuring probe having a hollow needle with a measuring section having a length, a partial section of the length being adapted for penetration into the body and in which a wall of the hollow needle is permeable to interstitial liquid surrounding the hollow needle within the body and an optical fiber including a measuring section that extends inside the hollow needle in the measuring section thereof and by which light is passed, the wavelength of the light being between 7 µm and 15 µm, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte and a measuring and evaluation unit to measure the modification and to derive, on the basis of the modification, information concerning the presence of the analyte in the body.

54. The device of claim 53 wherein the wavelength of the light is between 7 µm and 13 µm.

55. The device of claim 53 wherein the cross section of the optical fiber varies along the measuring section.

56. The device of claim 53 wherein only one optical fiber track runs inside the hollow needle in the measuring section, a distal end of the fiber track being provided with a mirror which reflects the light back along the same optical fiber track.

57. The device of claim 53 wherein two parallel optical fiber tracks extend in the hollow needle in the measuring section, wherein the light is transported through a one optical fiber track towards a distal end of the hollow needle and is deflected at the distal end of the hollow needle to return through the other optical fiber track.

58. The device of claim 57 wherein a prismatic reflector is arranged at the distal end of the hollow needle to deflect the light.

59. The device of claim 53 wherein the optical fiber is surrounded, at least in the measuring section, by a coating.

60. The device of claim 59 wherein the coating is metallic.

61. The device of claim 59 wherein the coating is a polymer.

62. The device of claim 59 wherein the coating consists essentially of synthetic diamond including diamond like carbon.

63. The device of claim 59 wherein the coating has an index of refraction which is at least as large as that of the optical fiber.

64. The device of claim 63 wherein the membrane is arranged within the hollow needle.

65. The device of claim 63 wherein the membrane is essentially separated from the surface of the optical fiber.

66. The device of claim 64 wherein the separation is effected by a coating on the optical fiber.

67. The device of claim 65 wherein the separation is effected by a metallic wire travelling in the longitudinal direction within the hollow needle between the optical fiber and the membrane.

68. The device of claim 65 wherein the separation is effected by a substrate having a cross sectional dimension projecting past the dimension of the optical fiber.

69. The device of claim 63 wherein the membrane is based on polycarbonate.

70. The device of claim 53 wherein the measuring section of the optical fiber is jacketed by a semi-permeable membrane such that the interstitial liquid in the measuring section only gains access to a surface of the optical fiber through the membrane.

71. The device of claim 53 wherein the interaction of the light transported in the optical fiber with the interstitial liquid is due to a penetration of an evanescent field into the interstitial liquid.

72. The device of claim 53 further comprising a light source that comprises at least one quantum cascade laser.

73. The device of claim 53 wherein the material of the optical fiber is selected from the group consisting of silver halide, chalcogenic glass, synthetic diamond, diamond-like carbon, silicon, and germanium.

74. The device of claim 53 wherein the optical fiber is fashioned from a layer produced by deposition from a gas phase onto a substrate.

75. The device of claim 53 wherein the optical fiber is integrated together with a substrate into the hollow needle.

76. The device of claim 53 wherein a light guide fiber, having a hardness which is less than that of the material from which the optical fiber is made, is joined to the optical fiber by pressing.

77. The device of claim 53 wherein a temperature measuring element is disposed on the optical fiber near a proximal end of the hollow needle.

78. Analysis device for determining an analyte in vivo in the body of a patient, the device comprising:

a measuring probe having a hollow needle with a measuring section having a length, a partial section of the length being adapted for penetration into the body and in which a wall of the hollow needle is permeable to interstitial liquid surrounding the hollow needle within the body and an optical fiber including a measuring section that extends inside the hollow needle in the measuring section thereof and by which light is passed, the wavelength of the light being between 7 µm and 15 µm, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte a measuring and evaluation unit to measure the modification and to derive, on the basis of the modification, information concerning the presence of the analyte in the body and a heating element and a temperature measuring element disposed on the optical fiber near a proximal end of the hollow needle.

79. Analysis device for determining an analyte in vivo in the body of a patient, the device comprising:

a measuring probe having a hollow needle with a measuring section having a length, a partial section of the length being adapted for penetration into the body and in which a wall of the hollow needle is permeable to interstitial liquid surrounding the hollow needle within the body and an optical fiber including a measuring section running inside the hollow needle in the measuring section thereof and by which light from a light source coupled to said fiber is passed, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte and a measuring and evaluation unit to measure the modification and to derive, on the basis of the modification, information concerning the presence of the analyte in the body, wherein the optical fiber is surrounded, at least in the measuring section, by a coating.

80. The device of claim 79 wherein the coating is metallic.

81. The device of claim 79 wherein the coating is a polymer.

82. The device of claim 79 wherein the coating has an index of refraction which is at least as large as that of the optical fiber.

83. Analysis device for determining an analyte in vivo in the body of a patient, the device comprising:

a measuring probe having a hollow needle with a measuring section having a length, a partial section of the length being adapted for penetration into the body and in which a wall of the hollow needle is permeable to interstitial liquid surrounding the hollow needle within the body and an optical fiber including a measuring section that extends inside the hollow needle in the measuring section thereof and by which light is passed from a light source, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte and a measuring and evaluation unit to measure the modification and to derive, on the basis of the modification, information concerning the presence of the analyte in the body, wherein the interaction of the light transported in the optical fiber with the interstitial liquid is due to a penetration of an evanescent field into the interstitial liquid surrounding the circumferential surface of the optical fiber.

84. Analysis device of claim 83 wherein the cross section of the optical fiber varies along the measuring section.

85. Analysis device of claim 83 wherein only one optical fiber track runs inside the hollow needle in the measuring section, the distal end of the fiber track being provided with a mirror which reflects the light back along the same optical fiber track.

86. Analysis device of claim 83 wherein two parallel optical fiber tracks extend in the hollow needle in the measuring section, wherein the light is transported through the one optical fiber track towards a distal end of the hollow needle and is deflected at the distal end of the hollow needle to return through the other optical fiber track.

87. Analysis device of claim 86 wherein a prismatic reflector is arranged at the distal end of the hollow needle to deflect the light.

88. Analysis device of claim 83 wherein the optical fiber is surrounded, at least in the measuring section, by a coating.

89. Analysis device of claim 88 wherein the coating is metallic.

90. Analysis device of claim 88 wherein the coating is a polymer.

91. Analysis device of claim 88 wherein the coating consists essentially of synthetic diamond including diamond like carbon.

92. Analysis device of claim 88 wherein the coating has an index of refraction which is at least as large as that of the optical fiber.

93. Analysis device of claim 83 wherein the measuring section of the optical fiber is jacketed by a semi-permeable membrane such that the interstitial liquid in the measuring section only gains access to a surface of the optical fiber through the membrane.

94. Analysis device of claim 93 wherein the membrane is arranged within the hollow needle.

95. Analysis device of claim 93 wherein the membrane is essentially separated from the surface of the optical fiber.

96. Analysis device of claim 95 wherein the separation is effected by a coating on the optical fiber.

97. Analysis device of claim 95 wherein the separation is effected by a metallic wire travelling in the longitudinal direction within the hollow needle between the optical fiber and the membrane.

98. Analysis device of claim 95 wherein the separation is effected by a substrate having a cross sectional dimension projecting past the dimension of the optical fiber.

99. Analysis device of claim 93 wherein the membrane is based on polycarbonate.

100. Analysis device of claim 83 wherein the wavelength of the light from the light source is between 7 µm and 15 µm.

101. Analysis device of claim 83 the light is coupled in from a light source that comprises at least one quantum cascade laser.

102. Analysis device of claim 83 wherein the material of the optical fiber is selected from the group consisting of silver halide, chalcogenic glass, synthetic diamond, diamond-like carbon, silicon, and germanium.

103. Analysis device of claim 83 wherein the optical fiber is fashioned from a layer produced by deposition from a gas phase onto a substrate.

104. Analysis device of claim 103 wherein the optical fiber is integrated together with the substrate into the hollow needle.

105. Analysis device of claim 83 wherein a light guide fiber, having a hardness which is less than that of the material from which the optical fiber is made, is joined to the optical fiber by pressing.

106. Analysis device of claim 83 wherein a temperature measuring element is disposed on the optical fiber near the proximal end of the hollow needle.

107. Analysis device for determining an analyte in vivo in the body of a patient, the device comprising:
- a measuring probe having
  - a hollow needle with a measuring section having a length, a partial section of the length being adapted for penetration into the body and in which a wall of the hollow needle is permeable to interstitial liquid surrounding the hollow needle within the body and
  - an optical fiber including a measuring section that extends inside the hollow needle in the measuring section thereof and by which light is passed from a light source, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte
- a measuring and evaluation unit to measure the modification and to derive, on the basis of the modification, information concerning the presence of the analyte in the body, and
- a heating element and a temperature measuring element are disposed on the optical fiber near a proximal end of the hollow needle,
- wherein the interaction of the light transported in the optical fiber with the interstitial liquid is due to a penetration of an evanescent field into the interstitial liquid surrounding the circumferential surface of the optical fiber.

108. Analysis device for determining an analyte in vivo in the body of a patient, the device comprising:
- a measuring probe having
  - a hollow needle with a measuring section having a length, a partial section of the length being adapted for penetration into the body and in which a wall of the hollow needle is permeable to interstitial liquid surrounding the hollow needle within the body and
  - an optical fiber including a measuring section that extends inside the hollow needle in the measuring section thereof and by which light is passed from a light source, the light transported through the optical fiber being modified in the measuring probe by direct reagent free interaction with the interstitial liquid surrounding the measuring section of the optical fiber within the measuring section of the hollow needle, said modification of the light being characteristic of the presence of the analyte and
- a measuring and evaluation unit to measure the modification and to derive, on the basis of the modification, information concerning the presence of the analyte in the body,
- wherein the optical fiber is surrounded, at least in the measuring section, by a coating.

109. Analysis device of claim 108 wherein the coating is metallic.

110. Analysis device of claim 108 wherein the coating is a polymer.

111. Analysis device of claim 108 wherein the coating consists essentially of synthetic diamond including diamond like carbon.

112. Analysis device of claim 108 wherein the coating has an index of refraction which is at least as large as that of the optical fiber.

113. Analysis device of claim 108 wherein the coating is a semipermeable membrane having a cut-off for large molecules having a molecular size in excess of 5,000 Da.

114. Analysis device of claim 113 wherein the cut-off for large molecules is 1,000 Da.

\* \* \* \* \*